US00PP28584P2

(12) United States Plant Patent
Christianson

(10) Patent No.: US PP28,584 P2
(45) Date of Patent: Oct. 31, 2017

(54) ***PARROTIA* TREE NAMED 'CHRISHAVEN1'**

(50) Latin Name: *Parrotia persica*
Varietal Denomination: Chrishaven1

(71) Applicant: Kenneth G. Christianson, Burlington, WA (US)

(72) Inventor: Kenneth G. Christianson, Burlington, WA (US)

( * ) Notice: Subject to any disclaimer, the term of this patent is extended or adjusted under 35 U.S.C. 154(b) by 112 days.

(21) Appl. No.: 14/757,376

(22) Filed: Dec. 22, 2015

(51) Int. Cl.
*A01H 5/00* (2006.01)

(52) U.S. Cl.
USPC ..... Plt./216

(58) Field of Classification Search
USPC ..... Plt./216
CPC ..... A01H 5/00
See application file for complete search history.

*Primary Examiner* — Kent L Bell
(74) *Attorney, Agent, or Firm* — Penny J. Aguirre

(57) ABSTRACT

A new cultivar of *Parrotia* tree, 'Chrishaven1', that is characterized by its upright and columnar plant habit, its foliage that turns deep yellow in color (with apricot-red markings) in the fall, its strong angled branches that withstand wind and snow, its strong apical dominance, and its ability to be readily propagated from stem cuttings.

3 Drawing Sheets

Genus/species: *Parrotia persica.*
Varietal denomination: 'Chrishaven1'.

BACKGROUND OF THE INVENTION

The present invention relates to a new and distinct cultivar of *Parrotia persica* and will be referred to hereafter by its cultivar name, 'Chrishaven1'. 'Chrishaven1' represents a new cultivar of Persian ironwood, a deciduous tree grown for landscape use.

The Inventor discovered the new cultivar in March of 1992 as a chance seedling that was growing in a field trial plot field that was planted from seed derived from unnamed and unpatented plants of *Parrotia persica* in Burlington, Wash.

Asexual propagation of the new cultivar was first accomplished in 2004 by grafting 'Chrishaven1' scion wood onto *Parrotia persica* (unpatented plant) understock. Subsequently, asexual propagation was performed by softwood stem cuttings under the direction of the Inventor in Burlington, Wash. in 2009. Asexual propagation by grafting and softwood stem cuttings has determined that the characteristics of the new cultivar are stable and are reproduced true to type in successive generations.

SUMMARY OF THE INVENTION

The following traits have been repeatedly observed and represent the characteristics of the new *Parrotia*. These attributes in combination distinguish 'Chrishaven1' as unique and distinct cultivar of *Parrotia.*

1. 'Chrishaven1' exhibits an upright and columnar plant habit.
2. 'Chrishaven1' exhibits foliage that turns deep yellow in color (with apricot-red markings) in the fall.
3. 'Chrishaven1' exhibits strong angled branches that withstand wind and snow.
4. 'Chrishaven1' exhibits strong apical dominance.
5. 'Chrishaven1' is readily propagated from stem cuttings.

Typical plants of the species *Parrotia persica*, differ from 'Chrishaven1' in having a broadly round plant habit and in having variable yellow to orange-red in the fall. 'Chrishaven1' can also be most closely compared to the cultivars *Parrotia* 'Vanessa' (not patented) and *Parrotia* 'Persian Spire' (not patented). 'Vanessa' is similar to 'Chrishaven1' in having an upright plant habit when young in age. 'Vanessa' differs from 'Chrishaven1' in developing a broader vase-shaped plant habit as the tree ages, in having weaker angled branches and in having fall color foliage that is typical to the species. 'Persian Spire' is similar to 'Chrishaven1' in having a columnar plant habit. 'Persian Spire' differs from 'Chrishaven1' in having a lower vigor and in having .wide leaf margins that are purple in color.

BRIEF DESCRIPTION OF THE DRAWINGS

The accompanying photographs were taken of ten year-old plants of 'Chrishaven1' as grown in a garden in Burlington, Wash.

The photograph in FIG. 1 provides a view of the fall foliage and plant habit of 'Chrishaven1'.

Figure 1:
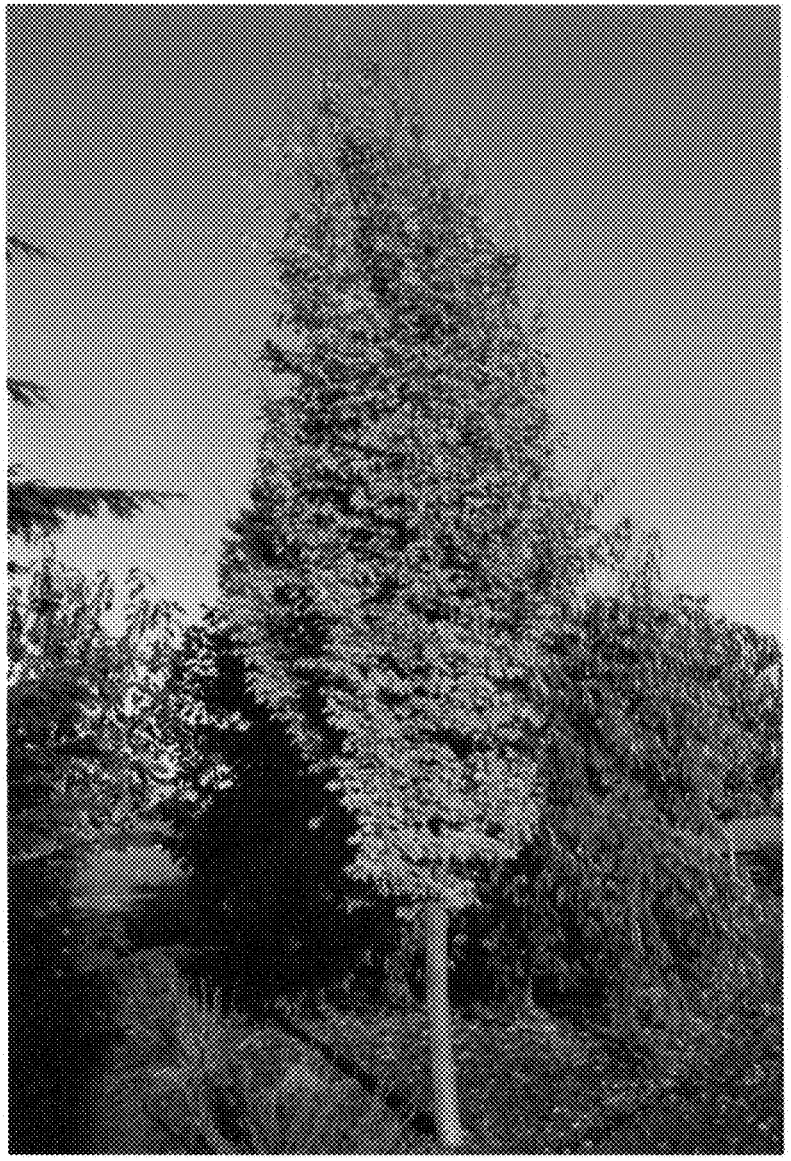
Figure 2:
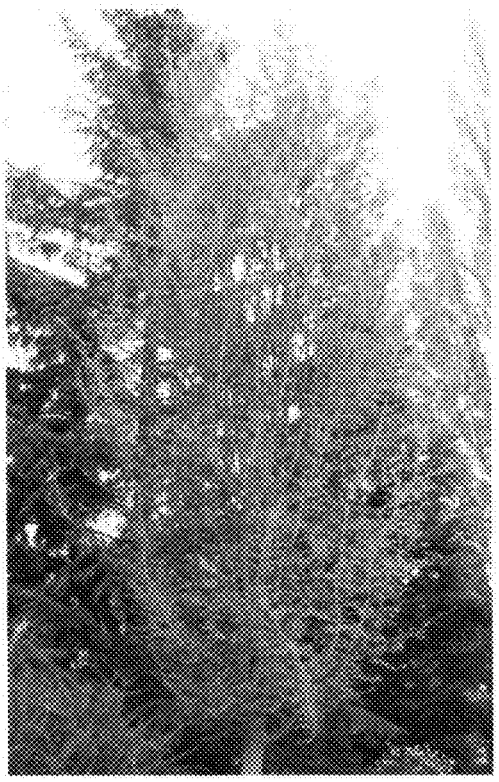

The photograph in FIG. 2 provides a view of the summer foliage of 'Chrishaven1'.

Figure 3:
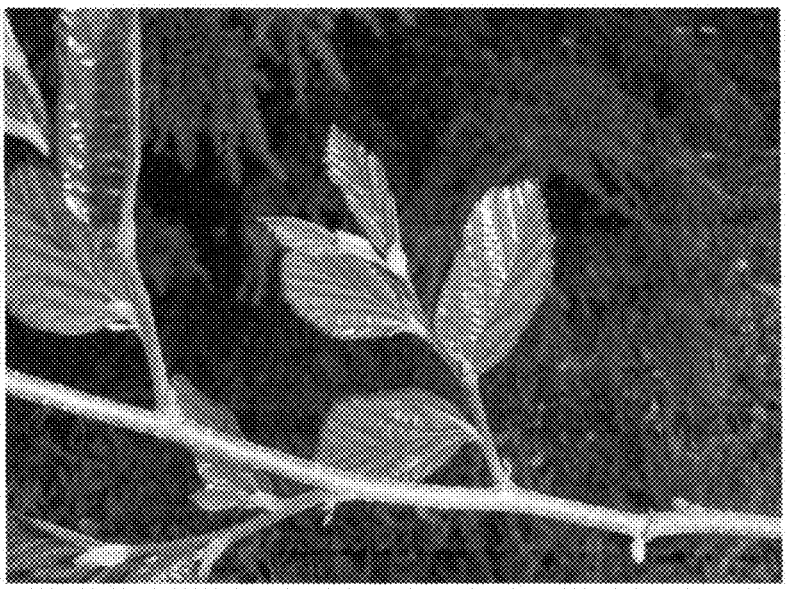

The photograph in FIG. 3 provides a close-up view of the new foliage of 'Chrishaven1'.

Figure 4:
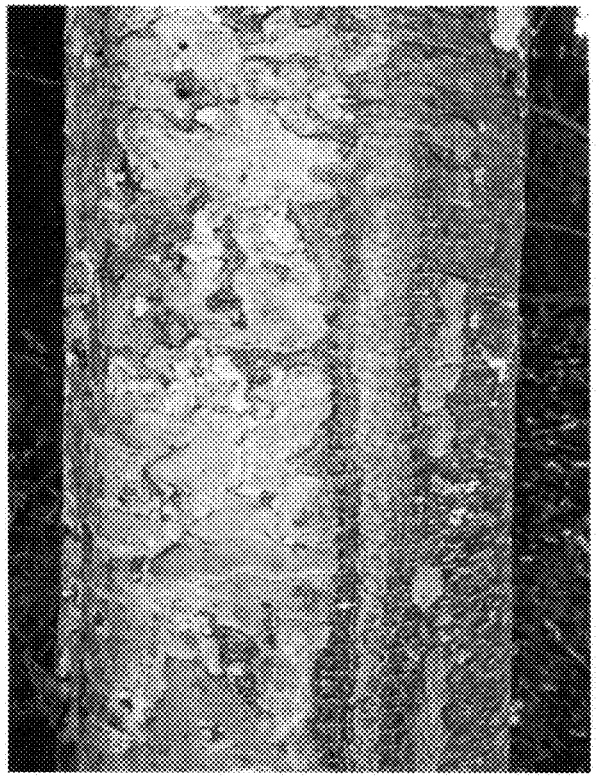

The photograph in FIG. 4 provides a view of the exfoliated bark of 'Chrishaven1'.

Figure 5:
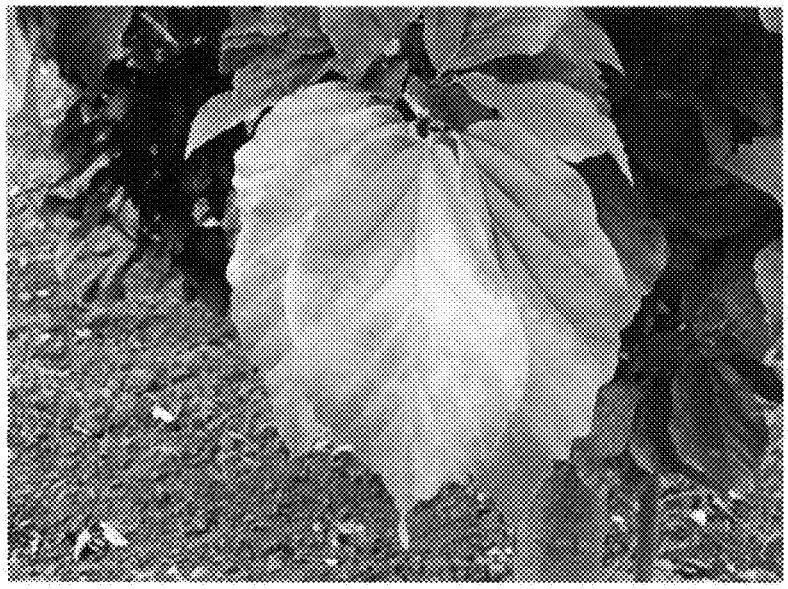

The photograph in FIG. 5 provides a view of leaves in fall (starting to turn color) of 'Chrishaven1'.

The colors in the photographs are as close as possible with the digital photography and printing techniques utilized and the color codes in the detailed botanical description accurately describe the colors of the new *Parrotia.*

BOTANICAL DESCRIPTION OF THE PLANT

The following is a detailed description of ten year-old plants (grafted in 2004) of the new cultivar as grown outdoors in a garden in Burlington, Wash. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Plant habit*.—Deciduous tree.

*Plant habit*.—Oval columnar with strong branch angles.

*Height and spread*.—An average of 6 m in height and 2.5 m in spread (as a ten year-old plant in the landscape).

*Hardiness*.—At least in U.S.D.A. Zone 4.

*Diseases and pests*.—No particular problems due to disease or insect pests have been observed to date.

*Growth rate*.—Moderate.

Branch description:

*Trunk size*.—Average of 10.6 cm in diameter measured 15 cm from soil line.

*Stem color*.—New growth (shoots) 178A in color; mature wood between 202C to 201A to 197A; older trunk and branches show mottled exfoliated bark between 202B to 202C and 200D and 164D.

*Stem shape*.—Round.

*Stem size*.—Lateral branches; average of 2.6 cm in diameter and 2 m in length, tertiary branches; an average of 59 cm in length and 5.4 mm in diameter.

*Stem surface*.—New growth; glabrous and lenticillate, old growth twigs; glabrous, lenticillate, mature bark; dull and exfoliating, lenticels; numerous, oblong in shape, 159A in color, about 2 mm in length and 1 mm in width, about 12 per areas 4 cm in length and 1 cm in width.

*Branching*.—Densely branched; lateral branch angles are less than 45° from vertical.

*Buds*.—4.5 mm in length and 2 mm in width, conical in shape, 159A in color, pubescent surface, tertiary stems; an average of 6.4 cm.

Foliage description:

*Leaf shape*.—Ovate.

*Leaf division*.—Simple.

*Leaf base*.—Rounded and slightly cordate.

*Leaf apex*.—Acuminate to acute.

*Leaf venation*.—Pinnate, upper surface same as leaf color, lower surface color 148D.

*Leaf margin*.—Crenate.

*Leaf attachment*.—Petiolate.

*Leaf arrangement*.—Alternate.

*Leaf surface*.—Glabrous and smooth on upper and lower surfaces, lower surface has pubescence on veins.

*Leaf size*.—Up to 9.8 cm in length and 5.8 cm in width.

*Leaf internode length*.—An average of 1.3 cm.

*Leaf color*.—New growth upper surface; 144A with very narrow margin of 59A, new growth lower surface; 146C, mature foliage upper surface; N137B to N137C, mature foliage lower surface; 147B, fall foliage upper and lower surface; 15A with markings between 22A, 34C and 45D, winter foliage upper and lower surface; primarily a blend of 162A and 176B.

*Petioles*.—Average of 5 cm in length and 1.8 mm in width, oval in shape, 178A in color, surface glabrous.

Flower description:

*Inflorescence*.—Apetalous clusters at terminus of axillary branches, not showy or distinguishable from typical flowers of the species.

*Blooming period*.—February 1 to March 1 in Burlington, Wash., prior to foliage breaking bud.

*Inflorescence size*.—Average of 3 cm in length and 1.9 cm in depth.

*Flower type*.—Perfect, apetalous.

*Flower fragrance*.—None.

*Flower size*.—Average of 1.5 cm in length and width when fully mature.

*Flower number*.—In dense clusters at tips of axillary branches, 2 to 4 flowers per cluster, up to 25 flowers per branch.

*Flower lastingness*.—About 3 weeks in Burlington, Wash.

*Flower buds*.—Ovate-globose in shape, an average of 5.3 mm in width, 6 mm in height and 202A in color, finely pubescent surface.

*Petals*.—Absent.

*Peduncles*.—An average of 1.7 cm in length and 1.75 mm in diameter, 144A in color, lightly suffused with 174A in color, glabrous surface.

*Pedicels*.—None.

*Perianth*.—Not present.

*Sepals*.—4, oblong-elliptic to lanceolate in shape, an average of 6 mm in length and 5 mm in width, acute apex, truncate base, surface is finely pubescent on upper surface and pubescent with long hairs on lower surface, color upper surface 147D, color lower surface 147A with hairs 202A.

*Bracts*.—4, elliptic-oblong in shape, up to 1 cm in length and 6 mm in width, cuspidate apex, truncate base, color on upper surface 147D, color on lower surface a blend of 202A and 147A, surface is finely pubescent on upper surface and pubescent with long hairs 202A in color on lower surface.

Reproductive organs:

*Stamens*.—An average of 40, anthers; 3 mm in length, 61B and changing to 183A in color when mature, filaments; 1 cm in length, very fine, 145D in color, pollen; moderate in quantity and 22A in color.

*Pistils*.—1, style: 2-branched, 145D in color, about 3 mm in length, stigmas; not discernable, ovary about 5 mm in length, oblong in shape, 145D in color.

*Fruit and seed*.—Capsule; 2-parted, N200A in color, an average of 8.2 mm in length and width, 165B in color, seed; average of 2 per capsule, round in shape, 202A in color, 4 mm in length and width.

It is claimed:

1. A new and distinct cultivar of *Parrotia* tree named 'Chrishaven1' substantially as herein illustrated and described.

* * * * *